(12) United States Patent
Bluth et al.

(10) Patent No.: US 6,403,897 B1
(45) Date of Patent: Jun. 11, 2002

(54) SEAT SCALE FOR HEALTH CARE MEASUREMENT KIOSK

(75) Inventors: Charles Bluth, Incline Village, NV (US); James Bluth, Verdi, CA (US); Raymond G. Bryan, Reno, NV (US); Jim C. Lovell, Sparks, NV (US); Richard L. Hicksted, Incline Village, NV (US); Michael A. Spahr, Reno, NV (US)

(73) Assignee: Computerized Screening, Inc., Sparks, NV (US)

( * ) Notice: Subject to any disclaimer, the term of this patent is extended or adjusted under 35 U.S.C. 154(b) by 0 days.

(21) Appl. No.: 09/548,805

(22) Filed: Apr. 14, 2000

(51) Int. Cl.[7] .................. G01G 19/52; G01G 19/00; A47B 83/02; A61B 5/00
(52) U.S. Cl. .................. 177/144; 177/245; 600/301; 297/138; 297/143; 297/158.2; 128/920
(58) Field of Search .................. 177/144, 245; 297/138, 143, 158.2; 600/301; 128/920

(56) References Cited

U.S. PATENT DOCUMENTS

| | | | | |
|---|---|---|---|---|
| 4,013,135 A | * | 3/1977 | Kechely .................. | 177/144 |
| 4,582,151 A | * | 4/1986 | Mairot et al. .................. | 177/144 |
| 4,799,562 A | * | 1/1989 | Burrows et al. .................. | 177/144 |
| 5,140,991 A | | 8/1992 | Niwa .................. | 128/687 |
| 5,380,269 A | * | 1/1995 | Urso .................. | 177/144 |
| D371,844 S | * | 7/1996 | Sadritabrizi et al. .................. | D24/165 |
| 5,801,755 A | * | 9/1998 | Echerer .................. | 348/13 |
| 5,918,696 A | * | 7/1999 | VanVoorhies .................. | 177/144 |
| 6,046,761 A | * | 4/2000 | Echerer .................. | 348/13 |

FOREIGN PATENT DOCUMENTS

| | | | | |
|---|---|---|---|---|
| EP | 0 422 512 | 4/1991 | .................. | A61B/5/022 |
| WO | WO 95/18564 | 7/1995 | .................. | A61B/5/00 |

* cited by examiner

Primary Examiner—Randy W. Gibson
(74) Attorney, Agent, or Firm—Skjerven Morrill MacPherson LLP (57) ABSTRACT

A health care test kiosk includes a carrel body, a controller, a physiological test interface, a seat, and a weight scale. The carrel body supports a console housing and includes a support side panel forming a lateral side and extending beyond the console housing. The controller is housed within the console housing and includes a display and user interface. The physiological test interface is coupled to and supported by the carrel body on the support side panel. The physiological test interface is communicatively coupled to the controller for supplying physiological information to the controller for analysis and display. The seat is coupled to the support side panel of the carrel body. The weight scale is coupled to and supported by the seat. The weight scale is communicatively coupled to the controller for supplying weight information to the controller for analysis and display in combination with the physiological data.

22 Claims, 6 Drawing Sheets

SEAT SCALE FOR HEALTH CARE MEASUREMENT KIOSK

BACKGROUND OF THE INVENTION

The field of medicine has long employed health care screening to diagnose and tract patients' health. An annual physical examination is a well-known part of patient medical care.

Hospitals, health clinics, and pharmacies, in addition to an active role is supplying medical supplies and pharmaceuticals, have actively promoted various health care screenings and wellness programs. Programs are sometimes offered with the help of other health care providers or coordinated on a national basis with groups such as the American Lung Association, the American Diabetes Association and the American Podiatric Medical Association.

To increase attention to the health care screening category, many medical and health produce retailers offer medical tests and screening for consumers visiting their stores. Most commonly, the retailers check cholesterol levels and blood pressure, although many other tests are available. In addition to supplying a valuable customer service, in-store testing effectively educates consumers about various health problems that can be better managed by a regimen that includes monitoring. Typically consumers are unaware of the technological advances that have made health care screenings feasible in the clinical, retail, and home settings. Pharmacies and drug retailers have generally found that point out that the availability of screening test devices in the stores increases traffic and cultivates customer loyalty.

The offer of in-store testing commonly is highly popular among customers and greatly boosts the number of people visiting the store. In-store testing is valuable for positioning stores as health and wellness centers as well as retailers of health care products. In-store testing increases sales since a consumer who learns of a health problem through screening in the store has some likelihood of purchasing a home test kit to monitor the problem. For example, a customer who discovers a problem of high blood pressure through an in-store test is a likely candidate to purchase a home test kit.

In-store health care screening expands the pharmacist's role in patient care through education. Test device manufacturers have advanced the design and functionality of products to simplify usage and improve accuracy. The challenge for further improvements in health care screening is to educate consumers about the need for medical tests, and demonstrate that many tests are effectively performed by publicly available devices or at home.

A present concern is that health screening is performed on an insufficient segment of the population to efficiently prevent or treat ailments. Other concerns are that health screening is too costly, limited in scope, and time-consuming both for individual patients and health care providers. Despite these deficiencies, a strong awareness exists of a need and desire for improved health screening procedures and equipment. Health care providers, insurance companies, and employers that ultimately pay for health care have encouraged development and usage of improved, accurate yet economic health screening facilities both for treatment and prevention of health care problems.

Generally individual doctors and small groups of doctors have insufficient capital to maintain a complete health screening facility. Even if more health care providers were suitably equipped, typically only a small part of the population exploits health screening facilities due to time and cost considerations and apathy.

Health screening devices and facilities, to be most useful to the public in general, should have a capability to serve a wide range of patient and user needs and situations. For example, health screening devices that perform fitness testing including cardiovascular testing and weight measurement are highly useful for assessing physical fitness.

What is needed is a health screening device or facility that allows physiological testing and physical measurements such as weight measurements at a single test session using a single test apparatus.

SUMMARY

According to one aspect of the present invention, a health care test kiosk includes a carrel body, a controller, a physiological test interface, a seat, and a weight scale. The carrel body supports a console housing and includes a support side panel forming a lateral side and extending beyond the console housing. The controller is housed within the console housing and includes a display and user interface. The physiological test interface is coupled to and supported by the carrel body on the support side panel. The physiological test interface is communicatively coupled to the controller for supplying physiological information to the controller for analysis and display. The seat is coupled to the support side panel of the carrel body. The weight scale is coupled to and supported by the seat. The weight scale is communicatively coupled to the controller for supplying weight information to the controller for analysis and display in combination with the physiological data.

In accordance with an another aspect of the present invention, a seat assembly for use in a health care test kiosk includes a seat and a weight scale. The health care kiosk includes a carrel body supporting a console housing and having a vacant knee-space beneath the console housing. The carrel body includes a support side panel forming a lateral side and extending beyond the console housing and the knee-space. The health care test kiosk further includes a physiological test interface coupled to and supported by the carrel body on the support side panel. The seat assembly includes the seat and the weight scale. The weight scale is coupled to and supported by the seat, the weight scale being communicatively coupled to the controller for supplying weight information to the controller for analysis and display in combination with the physiological data.

BRIEF DESCRIPTION OF THE DRAWINGS

The features of the described embodiments believed to be novel are specifically set forth in the appended claims. However, embodiments of the invention relating to both structure and method of operation, may best be understood by referring to the following description and accompanying drawings.

DESCRIPTION OF THE EMBODIMENTS

Figure 1:
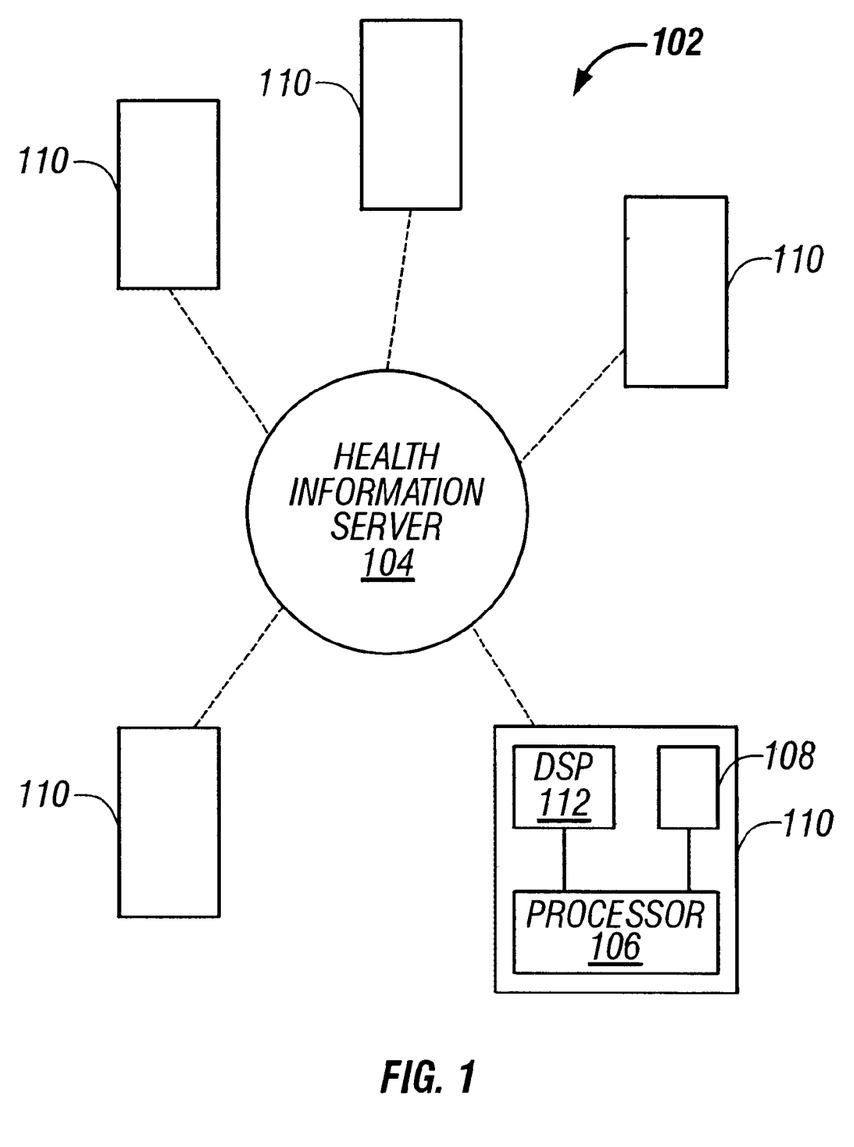
FIG. 1 is a schematic block diagram illustrating a suitable network for interconnecting one or more health care test kiosks and a health information server.

Referring to FIG. 1, a schematic block diagram illustrates a suitable network 102 for interconnecting one or more health care test kiosks 110 and a health information server 104. Typically, an individual health care test kiosk 110 includes a processor 106 or controller with a storage 108 or memory that maintains a local archive of user information that stores a relatively small number of relatively recent test results, measurements, and possibly other information. The processor 106 executes a logic (not shown), typically a computer program, that is stored as software, firmware, control logic or other executable forms as are known by one of ordinary skill in the art. In an illustrative health care information system 100, the health care test kiosk 110 employs additional computing power by adding a digital signal processor (DSP) 112 that operates in conjunction with the processor 106 to perform computation-intensive operations such as various health test operations.

The local archive includes tracking of health reading including blood pressure, heart rate and weight. Individual users also have an individual personal health site on the health information server 104. The health information server 104 is generally used to store a long-term archive of user results, measurements, and information received from the individual health care test kiosks 110. In one example, the local health care test kiosk 110 stores information from many users and all information that is generated on the health care test kiosk 110 is automatically loaded, for example on a daily basis, to the central health information server 104. The results are sent to the health information server 104 for long-term storage and archiving. The information for the individual users are stored on corresponding personal health sites that are assigned to the particular individual users so that accurate and current information are available for all of the individual users.

In the illustrative example, the individual users determine the degree and level of health care information to be acquired and stored on the site. The individual user assigns a privilege level to allow the user's physician to enter information to the site with a desired level of security. Using the secured access to the user's site, the physician can be allowed to download health care information to the user site. Information is not changed on the site so the physician's level of security insures accuracy of the downloaded information. The physician's security specification permits the physician to transmit secured prescription orders and records to the individual health care site.

The health care information system 100 benefits the individual users by permitting secured accessibility of health care information and prescription needs anywhere in the world through usage of the internet. The health care information system 100 supplies accurate and current individual health care information that is accessible in a crisis or emergency situation.

In one example, the health information server 104 includes a layered security program for protecting user data from privacy violations. In an example of a layered security program, a user's personal health site can have a sixteen digit security card for entry into the health care test kiosk 110 and an individual personal identification (PID) number to access the user's personal health site on the health information server 104. The level of security is equivalent to the security of an ATM machine in which the only person having access is the user since the user establishes the PID number.

The health care test kiosks 110 are generally accessible to the public. For example, pharmacies or drug stores are suitable facilities for supplying floor space for a health care test kiosk 110. Other suitable facilities include other retail outlets, health care providers such as physician offices, clinics, hospitals, and the like. The facilities housing a health care test kiosk 110 typically have an agreement with the kiosk supplier to supply information, services, and products. The health care test kiosk 110 executes various functions such as health testing and health evaluation. In some systems, the health care test kiosk 110 supports operations including health testing and measurement, health and fitness evaluation, and various health care information sources. Various health tests may be supported. Common health tests include blood pressure testing, heart rate testing, and the like. For example, some systems may support various non-invasive blood analyses using pulse oximetry data acquisition. Measurements may include simple or complex measurements. One common measurement is a weight measurement that is supplied using a seat scale 114 that is installed into the seat 116 of the health care test kiosk 110. A communication link 118 such as a bus, wire, or wireless link conveys weight information from the seat scale 114 to the processor 106. Patient or user weight information can be stored and accessed by the processor 106 for various health care and physiological analyses.

Health care information sources may include a drug encyclopedia, a vitamin and supplement encyclopedia, an electronic health care library, health care provider directories, and the like.

The health care test kiosk 110 interfaces to a server such as a store computer system or to a centralized server that services a wide geographical area. For example, the health care test kiosk 110 may interface to a local pharmacy or drug store computer. The health care test kiosk 110 may alternatively interface to a main frame health information server 104 that services a large area such as a country or region of the world. The health care test kiosk 110 in combination with the health information server 104 typically includes a highly comprehensive pharmacy library covering prescription drugs and over-the-counter remedies.

The individual health care test kiosks 110 commonly include display software that displays a selected idle presentation, an attract screen with still-frame or dynamic graphics, or plays video clips that promote a selected party such as the sponsoring store or medical service providers.

Software programs in the individual health care test kiosks 110 is updated by downloading, for example via internet access, or media transfer such as flexible disk loading.

The health information server 104 commonly supports Internet sites for user access of health information, storage of personal history information, and to shop for products that are not available local to the health care test kiosk 110.

Figure 2:
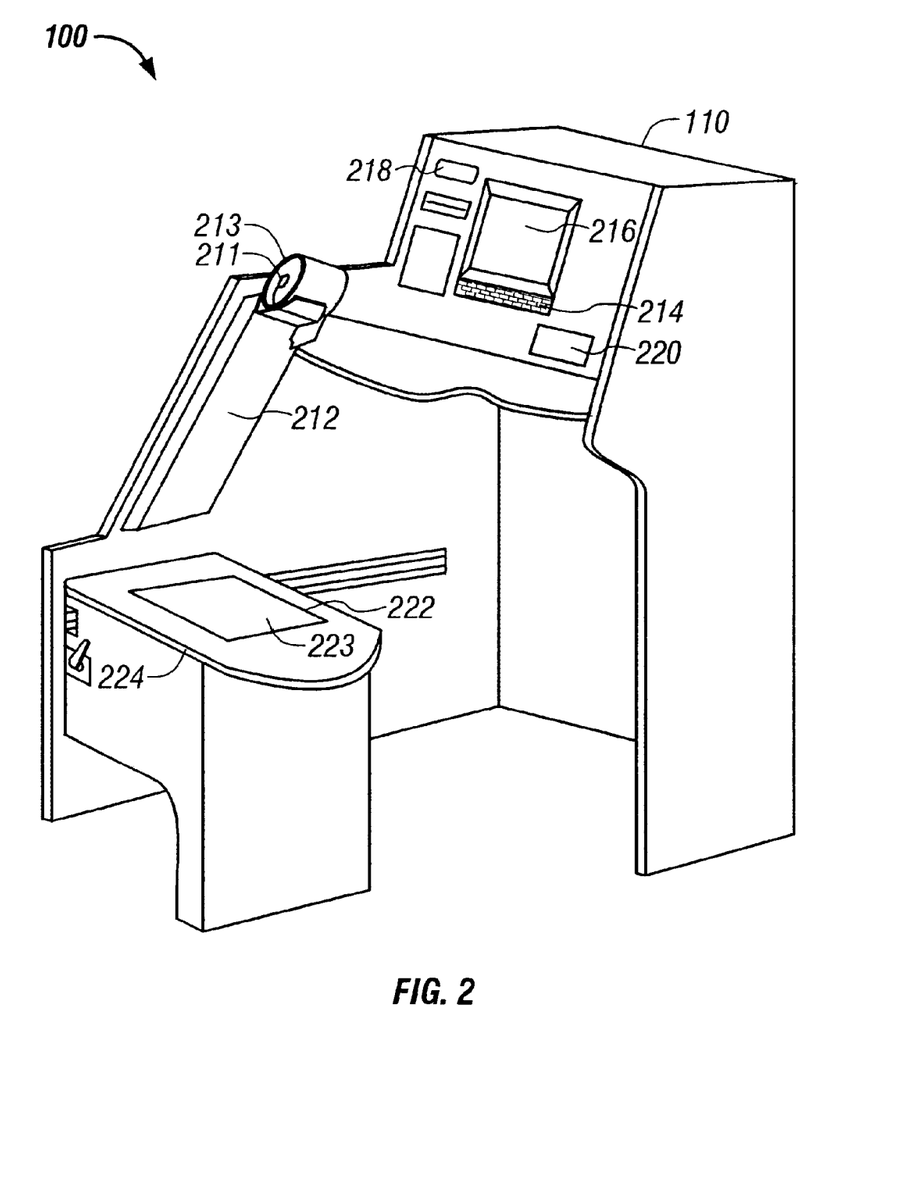
FIG. 2 is a pictorial diagram illustrating a suitable health care test kiosk for usage in interfacing to a health care information system.

Referring to FIG. 2, a pictorial diagram shows a suitable health care test kiosk 110 for usage in interfacing to a health care information system 100. The health care test kiosk 110 includes a test interface 212, a user interface 214, and a display 216. Some examples of the health care test kiosk 110 can include a measurement interface 222 that connects to a weighing scale 223. The test interface 212 and user interface 214 are connected to a processor 106 or controller that executes diagnostic test operations using data acquired using the test interface 212. In an illustrative example, the test interface 212 is a blood pressure cuff 213 for acquiring blood pressure measurements. A microphone 211 is attached to the blood pressure cuff 213 to measure a sound or audio signal. The user interface 214 is used to acquire patient data and other information that is entered by the user. The processor includes communication interfaces for communicating with the test interface 212, the user interface 214, the measurement interface 222, and a remote terminal so that the health care test kiosk 110 can be connected into a communication network (not shown). In some systems, the health care information system 100 includes a telephone handset 218 that a user may employ to receive information from the health care information system 100 in privacy or for usage in telephone communication. The health care information system 100 typically analyzes and displays information that is confidential to a patient, including medication lists, test diagnoses, physiological information, weight, age, illnesses, and the like. A user may be more comfortable having the information expressed using a private technique, such as a telephone receiver, than by a visual display that can be viewed by anyone in the vicinity of the health care test kiosk 110. Some versions of the health care test kiosk 110 optionally include a printer 220 for printing test results, information materials, advertisements, coupons, and the like.

The illustrative test interface 212 is a blood pressure cuff 213 with one or more pressure transducers (not shown) for acquiring blood pressure waveforms from the user. The pressure transducer has an electrical connection to the processor via the communication interface so that pressure waveform data is supplied to the processor. The processor executes a computerized blood pressure detection algorithm to produce highly accurate measurements of systolic and diastolic blood pressure, and mean blood pressure. The processor also analyzes the blood pressure waveforms to detect heart rate information.

The processor executes software programs including data analysis routines that produce highly accurate blood pressure and heart rate measurements. The health care information system 100 acquires other health care information from the patient, from physiological and measurement test interfaces connected to the patient, and from various health care databases via network communication linkages to generate a full health appraisal. The health care information system 100 includes local storage and the network communication link to external storage resources to allow a user to access pertinent health care information. For example, the health care information system 100 permits the user to access a full drug encyclopedia that lists pharmaceutical drugs that are currently available on the market. A health care provider directory is accessible via the network interconnection, either on the kiosk or by an Internet connection, to enable the user to find area physicians, specialists, clinics, hospitals, health maintenance organizations (HMOs), and the like.

One example of a suitable display 216 is a high-resolution Active Matrix color touchscreen display. The display 216 is used to present menus and controls, as well as to present information including test results, measurements, health information such as seasonal health tips. A text display shows text in one or more of various selected languages. Many other displays of various sizes, specifications, and utilizing various technologies are also suitable.

One example of a suitable test interface 212 is a blood pressure cuff 213 including a nylon washable exterior cuff with a seamless inner natural latex bladder that is inflated using a pneumatic power system. A suitable cuff size is 30×12.5 cm. The cuff can be constructed of medical grade silicone tubing that is non-reactive, and thus allergy-free, to body tissue. Cuff pressure is regulated by pressure monitors (not shown) that are inherently stable and are calibrated to function accurately with cuff pressure variations of less than +/−1% over a full operating range of systolic maximum pressure 250 mm-Hg and minimum pressure 80 mm-Hg, and diastolic maximum pressure 130 mm-Hg and minimum pressure 38 mm-Hg, a differentiation of 8 points between systolic and diastolic pressure, and a heart rate from 38 to 200 bpm. The monitors use automatic zero pressure variations to prevent accuracy from being affected by altitude level or other changes in atmospheric pressure, temperature, and humidity. The exemplary test interface 212 also detects sound signals for usage with Korotkoff sound detection. Both pressure signals and sound signals are converted to digital form and transmitted to the processor to perform blood pressure measurements using both oscillometric and auscultatory analysis. The pressure and sound signals can be processed to determine heart rate measurement using a beat-to-beat averaging method. In some examples, tests are activated using a touch screen in which a virtual green start button initiates a test procedure by inflating the cuff that the patient has positioned around the arm. Touching the display screen halts the test and returns the pneumatic cuff to the open position. Various other specifications, materials, and technologies or combinations of technologies that are known by those having ordinary skill in the art are also suitable.

An illustrative measurement interface 222 is a weighing scale 223 formed into a moveable seat 224 that is attached to the health care test kiosk 110. The measurement interface 222 carries measurement signals from measurement devices, such as the weighing scale 223, to the processor 106 for analysis and display. The measurement interface 222 also carries control, data, and other information, for example initialization information, to the measurement devices. In one example, the weighing scale 223 is a digital scale that is calibrated and initialized by signals transmitted from the processor 106. In one example, the seat weighing scale 223 has an accuracy within one pound. The seat 224 of the health care test kiosk 110 is moveable so that the test interface 212 and display 216 are wheel chair accessible and easily used by the disabled without assistance.

Figure 3A:
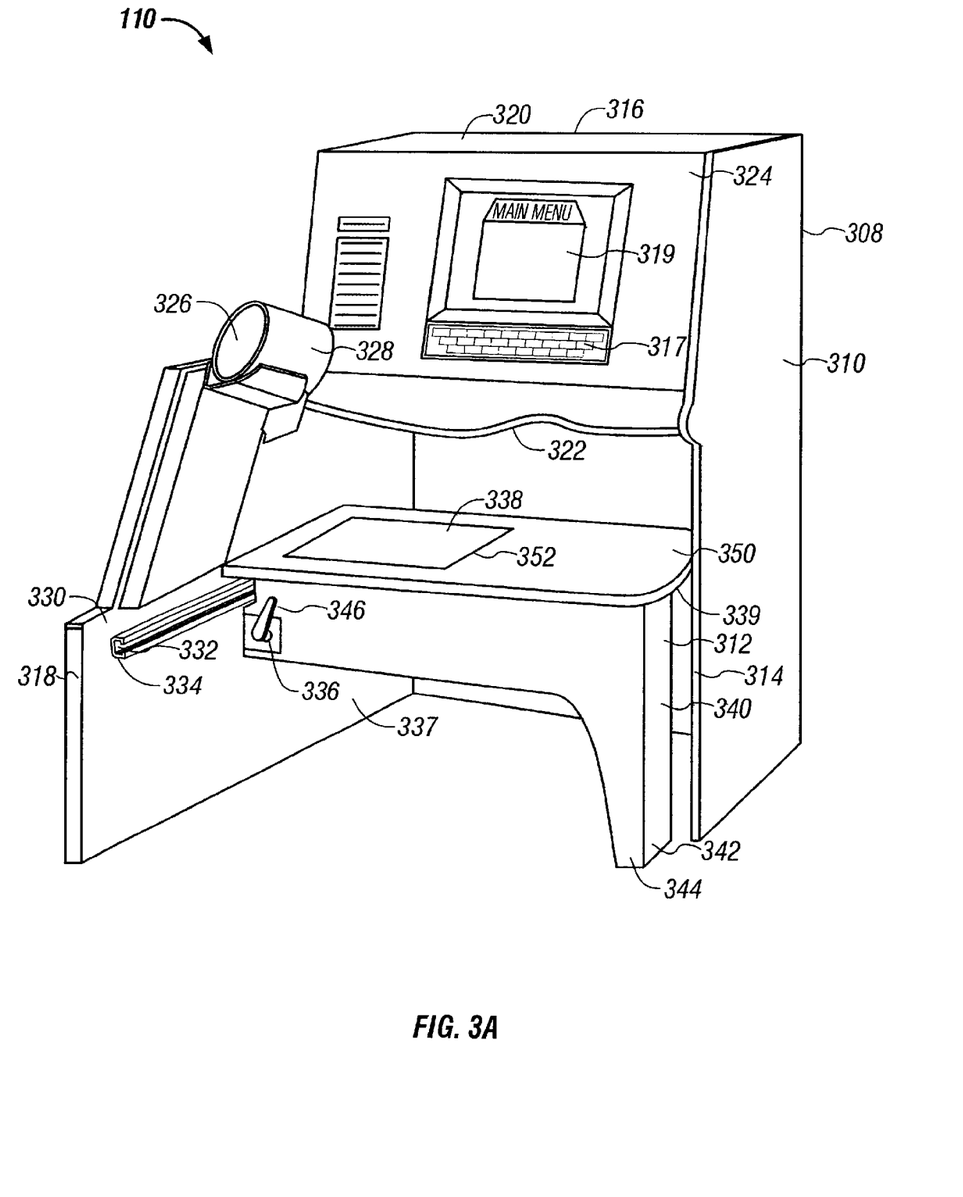
FIGS. 3A, 3B, 3C, and 3D are four three-dimensional pictorial diagrams showing various frontal views of a health care information kiosk with a retractable seat.
Figure 3B:
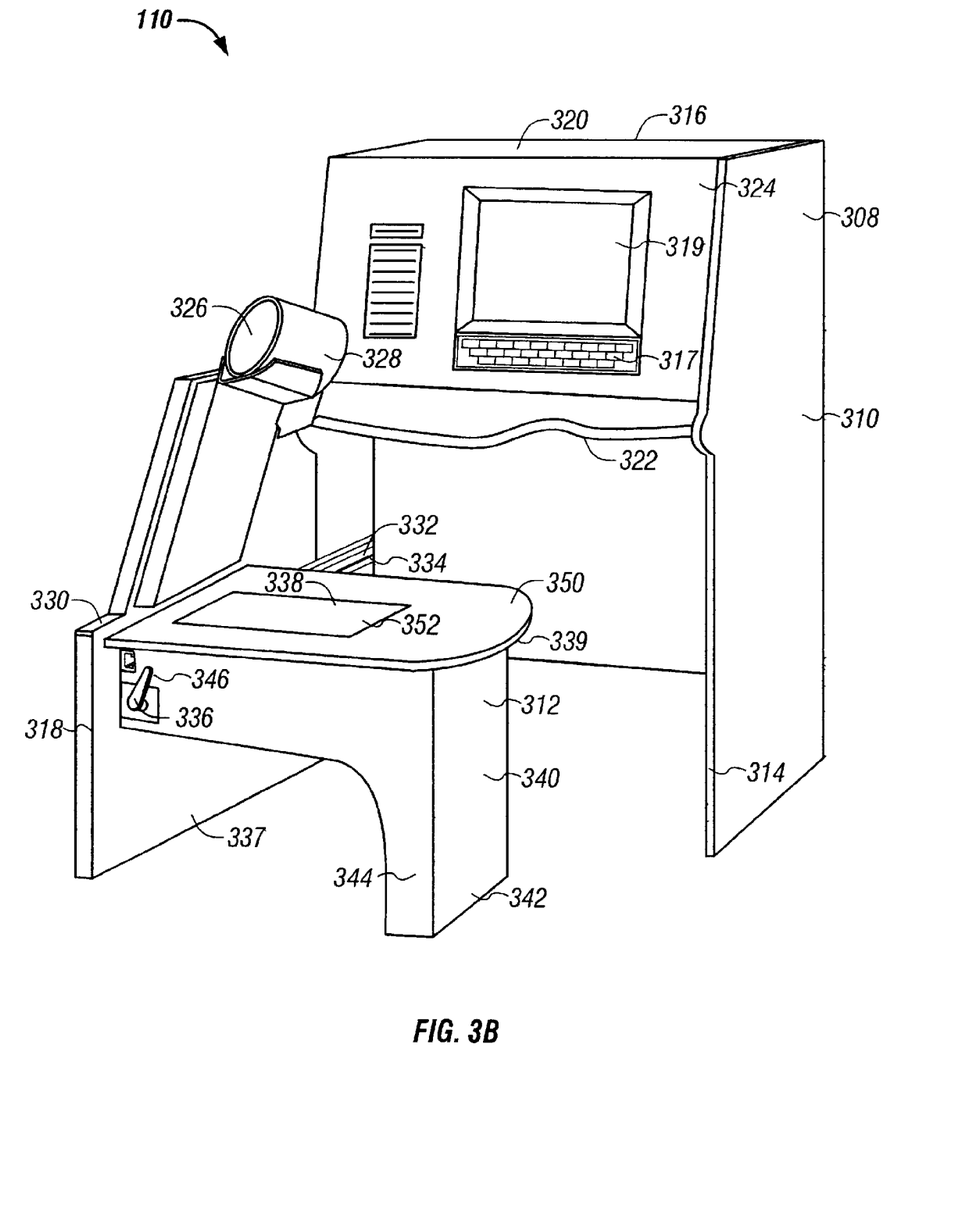
Figure 3C:
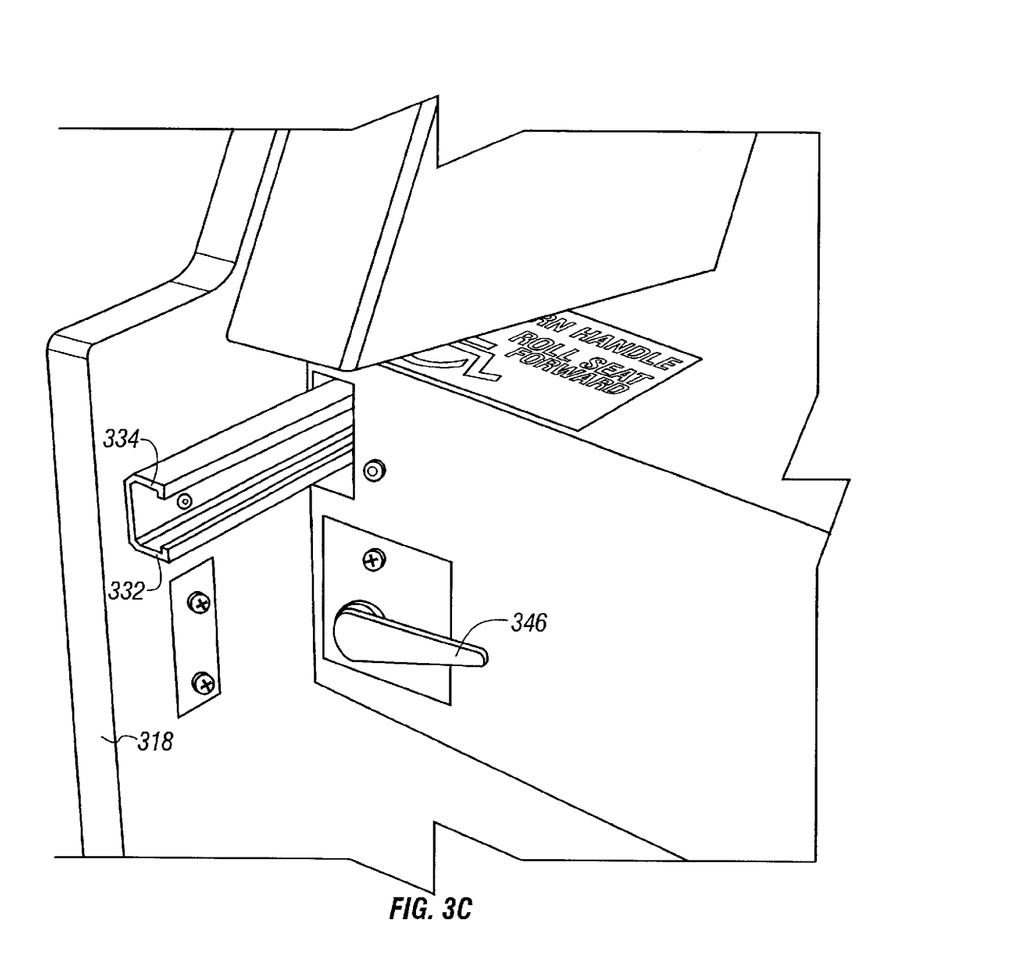
Figure 3D:
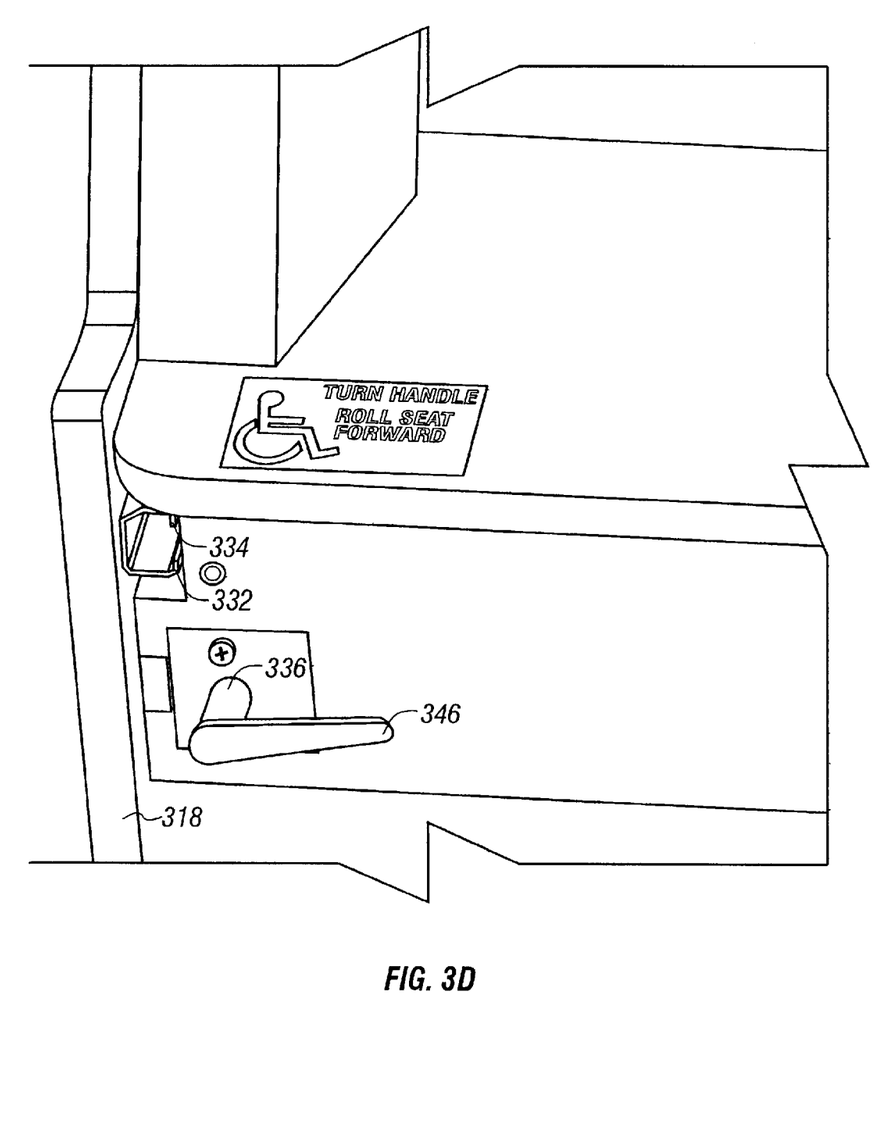

Referring to FIGS. 3A, 3B, 3C, and 3D, four three-dimensional pictorial diagrams show various frontal views of a health care information kiosk 110. FIG. 3A illustrates a frontal view of the fall health care information kiosk 110 with a retractable seat assembly 312 in an enclosed position within the kiosk. FIG. 3B illustrates a frontal view of the full health care information kiosk 110 with a retractable seat assembly 312 in a withdrawn from the enclosed position with respect to the kiosk. FIG. 3C shows a locking mechanism of the retractable seat assembly with the seat enclosed into the kiosk. FIG. 3D shows the locking mechanism of the retractable seat assembly 312 with the seat assembly in an extended position. The health care test kiosk 110 includes a carrel body 310 and a moveable and retractable seat assembly 312.

The carrel body 310 has an entry side panel 314 and a support side panel 318 that are opposing and connect at right angles to a back panel 316, forming three sides of a console housing 308. The console housing 308 contains a health care test controller (not shown) with input interface 317 and display 319 that respectively control a test acquisition and display a test result. The console housing 308 also includes a planar top panel 320 connected at right angles to top edges of the entry side panel 314, the back panel 316, and the support side panel 318. The console housing 308 also includes a planar bottom panel 322 that forms a plane parallel to the plane of the top panel 320 and is affixedly attached at a position medial to the top and bottom edges of the entry side panel 314, the back panel 316, and the support side panel 318. The bottom panel 322 is interposed at the medial position at a suitable height from the floor to allow sufficient vacant knee-space for a person seated on the seat assembly 312. The structure of the console housing 308 is completed by a display panel 324 that opposes the back panel 316, connects to edges of the top panel 320 and the entry side panel 314, connects to an edge and surface of the support side panel 318, and connects to a surface of the bottom panel 322. A portion of the bottom panel 322 extends forward beyond the display panel 324 to form a resting surface for the convenience of a user.

The support side panel 318 extends forward beyond the forward edges of the display panel 324 and the entry side panel 314. The support side panel 318 supports a physiological test structure 326 that, in the present example, is a blood pressure test interface 328. The physiological test structure 326 is moveable or positionable to permit testing of different sized users. For example, the illustrative physiological test structure 326 is connected to the support side panel 318 at a pivot point so that a test acquisition element, such as a blood pressure cuff, can be moved to various positions along a radius to allow testing of users ranging from large adults to small children. The moveable or positionable characteristics of the physiological test structure 326 are also useful for allowing test access to users in different positions. For example, a user in a wheel chair may position the seat assembly 312 in the knee-space beneath the console housing 308, move the wheel chair into a position near the physiological test structure 326, and pivot the physiological test structure 326 into a suitable position for acquiring a measurement.

The support side panel 318 has a mounting surface 330 upon which is mounted a seat track 332. In the illustrative health care test kiosk 110, the seat track 332 is an elongated bar with a C-shaped cross-sectional form 334. The seat track 332 extends longitudinally from front to back of the support side panel 318 in a horizontal configuration so that the seat assembly 312 that is movably attached to the health care test kiosk 110 can move horizontally beneath the console housing 308 and retracted forward from the console housing 308. The physiological test structure 326 is positioned so that the seat assembly 312 is clear from obstruction whether the seat assembly 312 is enclosed beneath the console housing 308 or extended from the console housing 308. A seat lock 336 is also affixed to the mounting surface 330 of the support side panel 318, typically positioned near a forward portion of the seat track 332. The seat lock 336 permits the seat assembly 312 to be held firmly in place when a user is using the health care test kiosk 110.

The illustrative seat assembly 312 has a top horizontal planar support 350 that is supported on a support side 337 by a moveable connection to the seat track 332 and supported on an entry side 339 by a fixedly attached seat support 340. The illustrative top horizontal planar support 350 is shown as a planar, level panel that is generally in the form of a rectangle except with corners rounded on the entry side of the health information kiosk 110. The top horizontal planar support 350 serves as a brace for holding a weighing scale 352 that measures the weight of a user. In some systems, the weighing scale 352 has a cable (not shown) that extends to the edge of the seat assembly 312 through an aperture (not shown) in the support side panel 318 to the console housing 308, then into the console housing 308 to the health care test controller. The cable may carry data signals, control signals, and power. In some systems, the cable may carry data and control signals alone and be powered by a battery. Some systems may communicate data and control signals using wireless techniques. Any combination of wired and wireless communication may be used.

A top seat panel 338 is supported by the weighing scale 352 and serves as a sitting surface for the user. The illustrative top seat panel 338 has the form of a planar, horizontal panel or flat bench-top panel. The top seat panel 338 in other examples may take various other forms. For example, instead of a planar surface, the top seat panel 338 may have a contoured top surface for comfort of the user.

In the exemplified seat support 340 includes a side seat support 342 and a front seat support 344 that are firmly attached at an angle, such as a right angle, that supports the top seat panel 338 in two dimensions. Top surfaces of the seat support 340 lie in a single plane and are fastened to the top seat panel 338. The seat assembly 312 is removably and retractably attached to the carrel body 310 by a moveable connector (not shown) that is firmly affixed to the top seat panel 338 and movably connects to the seat track 332. The seat assembly 312 is generally a suitable size to fit completely within the cavity beneath the console housing 308 when the seat assembly 312 is positioned in a withdrawn position.

In an illustrative example, the moveable connector is a horizontal bar (not shown) with a T-shaped cross-section so that the T-connector is movably held within the C-shaped cross-section of the seat track 332. In other suitable examples, the moveable connector may be a plurality of T-brackets (not shown) that are affixed at regular (or otherwise) intervals along the side of the top seat panel 338. In other examples, the seat track 332 may include a horizontally-disposed rod (not shown) that is disposed within one or more cylindrical hinges that are attached to the top seat panel 338 and have a hollow cylindrical central lumen encasing the rod. A lock handle 346 is attached to the seat assembly 312 and is operated to engage the seat lock 336. Other moveable attachment structures that are known to one having ordinary skill in the art may be used to movably connect the seat assembly 312 to the carrel body 310.

An alternative structure may include more than one seat lock 336 disposed at various positions on the support side panel 318 to selectively hold the seat assembly 312 at a plurality of positions. For example, one seat lock 336 may be disposed near the forward edge of the support side panel 318 to permit a large adult to sit a comfortable distance from the console housing 308. A second seat lock may be positioned a few inches back from the first seat lock to permit a smaller adult to more easily reach the console housing 308. A third seat lock may be positioned a few more inches back from the second seat lock to fit a child within the health care test kiosk 110. A seat lock may or may not be positioned at an innermost location closest to the back panel 316 so that the seat assembly 312 may be fully enclosed into the health care test kiosk 110 to permit a user in a wheel chair to use the physiological test structure 326. An inner seat lock may be omitted in consideration of allowing a weaker user to withdraw the seat assembly 312 without reaching beneath the carrel body 310 knee-space and having to disengage the lock. Alternatively, an inner seat lock may be employed to prevent the seat assembly 312 from inadvertently rolling from beneath the carrel body 310 knee-space and interfering with a wheel chair user.

While the invention has been described with reference to various embodiments, it will be understood that these embodiments are illustrative and that the scope of the invention is not limited to them. Many variations, modifications, additions and improvements of the embodiments described are possible. For example, those skilled in the art will readily implement the steps necessary to provide the structures and methods disclosed herein, and will understand that the process parameters, materials, and dimensions are given by way of example only and can be varied to achieve the desired structure as well as modifications which are within the scope of the invention. Variations and modifications of the embodiments disclosed herein may be made based on the description set forth herein, without departing from the scope and spirit of the invention as set forth in the following claims.

In the claims, unless otherwise indicated the article "a" is to refer to "one or more than one".

What is claimed is:

1. A health care test kiosk comprising:
   a carrel body supporting a console housing and including a support side panel forming a lateral side and extending beyond the console housing;
   a controller housed within the console housing and including a display and user interface;
   a physiological test interface coupled to and supported by the carrel body on the support side panel, the physiological test interface being communicatively coupled to the controller for supplying physiological information to the controller for analysis and display;
   a seat that is coupled to the support side panel of the carrel body, the seat including:
      a top horizontal planar support;
      a seat track; and
      a seat support,
         the top horizontal planar support being supported on the support side panel by a moveable connection to the seat track; and supported on an entry side by the fixedly attached seat support;
         the top horizontal planar support being a brace for holding the weight scale; and
   a weight scale coupled to and supported by the seat, the weight scale being communicatively coupled to the controller for supplying weight information to the controller for analysis and display in combination with the physiological data.

2. A health care kiosk according to claim 1 further comprising:
   a communication link such as a bus, wire, or wireless link coupling the weight scale to a controller to weight information from the weight scale to the controller.

3. A health care kiosk according to claim 1 wherein:
   the weight scale is a digital scale that is calibrated and initialized by signals transmitted from the controller.

4. A health care kiosk according to claim 1 wherein:
   the seat is a moveable seat; and
   the weight scale is formed into the moveable seat that is attached to the health care test kiosk.

5. A health care kiosk according to claim 1 wherein:
   the physiological interface carries measurement signals from measurement devices including the weighing scale to the controller for analysis and display.

6. A health care kiosk according to claim 1 wherein:
   the weight scale has an accuracy within one pound.

7. A health care kiosk according to claim 1 wherein:
   the top horizontal planar support has the form of a planar, level panel that is generally in the form of a rectangle except with comers rounded on the entry side of the health information kiosk.

8. A health care kiosk according to claim 1 further comprising:
   a cable coupling the weight scale to the controller, the cable carrying signals selected from among data signals, control signals, and power.

9. A health care kiosk according to claim 1 further comprising:
   a top seat panel supported by the weight scale and being a sitting surface for a user.

10. A health care kiosk according to claim 1 further comprising:
   a top seat panel supported by the weight scale and being a sitting surface for a user, the top seat panel having a form selected from among a planar form, a horizontal planar form, a flat bench-top panel form, and a contoured form.

11. A seat assembly for use in a health care test kiosk that includes a carrel body supporting a console housing and having a vacant knee-space beneath the console housing, the carrel body including a support side panel forming a lateral side and extending beyond the console housing and the knee-space, the health care test kiosk further including a physiological test interface coupled to and supported by the carrel body on the support side panel, the seat assembly comprising:
   a seat including:
      a top horizontal planar support;
      a seat track; and
      a seat support,
         the top horizontal planar support being supported on the support side panel by a moveable connection to the seat track; and supported on an entry side by the fixedly attached seat support;
         the top horizontal planar support being a brace for holding the weight scale; and
   a weight scale coupled to and supported by the seat, the weight scale being communicatively coupled to the controller for supplying weight information to the controller for analysis and display in combination with the physiological data.

12. A seat assembly according to claim 11 wherein:
   the seat assembly and the seat are retractable.

13. A seat assembly according to claim 11 further comprising:
   a communication link such as a bus, wire, or wireless link coupling the weight scale to a controller to weight information from the weight scale to the controller.

14. A seat assembly according to claim 11 wherein:
   the weight scale is a digital scale that is calibrated and initialized by signals transmitted from the controller.

15. A seat assembly according to claim 11 wherein:
   the seat is a moveable seat; and
   the weight scale is formed into the moveable seat that is attached to the health care test kiosk.

16. A seat assembly according to claim 11 wherein:
   the physiological interface carries measurement signals from measurement devices including the weighing scale to the controller for analysis and display.

17. A seat assembly according to claim 11 wherein:
   the weight scale has an accuracy within one pound.

18. A seat assembly according to claim 11 wherein:
   the top horizontal planar support has the form of a planar, level panel that is generally in the form of a rectangle except with comers rounded on the entry side of the health information kiosk.

19. A seat assembly according to claim 11 further comprising:
   a cable coupling the weight scale to the controller, the cable carrying signals selected from among data signals, control signals, and power.

20. A seat assembly according to claim 11 further comprising:
 a top seat panel supported by the weight scale and being a sitting surface for a user.

21. A seat assembly according to claim 11 further comprising:
 a top seat panel supported by the weight scale and being a sitting surface for a user, the top seat panel having a form selected from among a planar form, a horizontal planar form, a flat bench-top panel form, and a contoured form.

22. A method of fabricating a health care test kiosk comprising:
 forming a carrel body supporting a console housing and having a vacant knee-space beneath the console housing;
 attaching a support side panel as a side of the carrel body, the support side panel forming a lateral side and extending beyond the console housing and the knee-space;
 attaching a physiological test interface to the carrel body on the support side panel;
 movably coupling a retractable seat to the support side panel of the carrel body for selective positioning in a location ranging from withdrawn into the knee-space beneath the console housing to extended completely from the knee-space, the retractable seat including:
  a top horizontal planar support;
  a seat track; and
  a seat support;
 supporting the top horizontal planar support on the support side panel by a moveable connection to the seat track and on an entry side by the fixedly attached seat support;
 coupling the weight scale to the seat so that the seat supports the weight scale, the top horizontal planar support being a brace for holding the weight scale; and
 communicatively coupling the weight scale to the controller for supplying weight information to the controller for analysis and display in combination with the physiological data.

\* \* \* \* \*